US009008798B2

(12) United States Patent
Tangren et al.

(10) Patent No.: US 9,008,798 B2
(45) Date of Patent: Apr. 14, 2015

(54) PRE-LOADED VIBRATION ISOLATOR FOR IMPLANTABLE DEVICE

(71) Applicant: Cardiac Pacemakers, Inc., St. Paul, MN (US)

(72) Inventors: John H. Tangren, Lino Lakes, MN (US); Jean M. Bobgan, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/107,934

(22) Filed: Dec. 16, 2013

(65) Prior Publication Data

US 2014/0180372 A1 Jun. 26, 2014

Related U.S. Application Data

(60) Provisional application No. 61/745,277, filed on Dec. 21, 2012.

(51) Int. Cl.
*A61N 1/00* (2006.01)
*A61N 1/08* (2006.01)
*A61N 1/375* (2006.01)

(52) U.S. Cl.
CPC ............. *A61N 1/08* (2013.01); *A61N 1/3758* (2013.01)

(58) Field of Classification Search
USPC ........................................................ 607/116
See application file for complete search history.

(56) References Cited

U.S. PATENT DOCUMENTS

| 4,041,956 | A | 8/1977 | Purdy et al. |
| 4,243,042 | A | 1/1981 | Ware |
| 5,144,946 | A | 9/1992 | Weinberg et al. |
| 5,456,698 | A | 10/1995 | Byland et al. |
| 5,741,313 | A | 4/1998 | Davis et al. |
| 5,873,899 | A | 2/1999 | Stutz, Jr. et al. |
| 6,939,569 | B1 * | 9/2005 | Green et al. .................. 424/667 |
| 2004/0085251 | A1 * | 5/2004 | Shimura ....................... 343/872 |
| 2009/0287263 | A1 | 11/2009 | Dahl et al. |
| 2010/0194541 | A1 | 8/2010 | Stevenson et al. |
| 2013/0289663 | A1 * | 10/2013 | Newman ......................... 607/62 |
| 2014/0005569 | A1 * | 1/2014 | Miethke ........................ 600/561 |

FOREIGN PATENT DOCUMENTS

WO WO-2014099808 A1 6/2014

OTHER PUBLICATIONS

Murata, H., et al., "Dynamic viscoelastic properties and the age changes of long-term soft denture liners", Biomaterials, 21, (2000), 1421-1427.
Santawisuk, W., et al., "Dynamic viscoelastic properties of experimental silicone soft lining materials", Dental Materials Journal, 29(4), (2010), 454-460.

(Continued)

*Primary Examiner* — Robert N Wieland
(74) *Attorney, Agent, or Firm* — Schwegman Lundberg & Woessner, P.A.

(57) ABSTRACT

This document describes an apparatus or an implantable medical device including an implantably biocompatible case. The apparatus can include a component that can be sealed within the case. The apparatus can include a vibration isolator and an at least a portion of the vibration isolator can be situated between and compressively preloaded to bias against the case and the component.

19 Claims, 8 Drawing Sheets

(56) References Cited

OTHER PUBLICATIONS

"International Application Serial No. PCT/US2013/75451, International Search Report mailed Mar. 12, 2014", 4 pgs.

"International Application Serial No. PCT/US2013/75451, Written Opinion mailed Mar. 12, 2014", 7 pgs.

* cited by examiner

PRE-LOADED VIBRATION ISOLATOR FOR IMPLANTABLE DEVICE

CLAIM OF PRIORITY

This application claims the benefit of U.S. Provisional Application No. 61/745,277, filed on Dec. 21, 2012, which is incorporated herein by reference in its entirety.

CROSS REFERENCE TO RELATED APPLICATIONS

The present application is related to U.S. patent application Ser. No. 12/464,655, published as 2009/0287263, entitled "Medical Device with Liquid Filled Housing," filed on May 12, 2009, which is incorporated herein by reference in its entirety.

BACKGROUND

An implantable medical device can include a component holder, such as a circuit board retainer or a support structure, to retain one or more components (for example, electronic components mounted on a circuit board or other substrate, a capacitor, a battery, a feedthrough, or one or more combinations thereof). The component holder can undesirably permit gaps between the components and the retainer. A patient can create an external load on the one or more components causing them to undesirably move. The implantable medical device can be subjected to the external load during transportation or handling. The external load on the implantable medical device can cause the components to move and further cause stress in connections between the components. For example, movement of the circuit board can induce stress in electrical connections between the board and a feedthrough, the board and a battery, etc.

A support structure of molded thermoplastic foam surrounding the components of the implantable medical device within a case to provide the components with shock and vibration resistance is discussed in U.S. Pat. No. 5,873,899 entitled IMPLANTABLE MEDICAL DEVICE HAVING COMPLIANT SUPPORT FOR INTERNAL COMPONENTS.

Placement of adhesive compressible foam around and between the internal components of the stimulation device to stabilize the device against shock and vibration is discussed in U.S. Pat. No. 5,741,313 entitled IMPLANTABLE MEDICAL DEVICE WITH A REDUCED VOLUMETRIC CONFIGURATION AND IMPROVED SHOCK STABILIZATION.

OVERVIEW

The present inventors have recognized and believe that the above-mentioned approaches cannot withstand an environment where a relatively higher shock or vibration can be induced within the implantable medical device. Specifically, patients with implanted devices can be subjected to a magnetic resonance imaging (MRI) scan such as to diagnose one or more portions of the body. Electromagnetic radiations produced during the MRI scan can vibrate a device, such as through mechanically exciting components within the device with electromotive force. Any vibration can be undesired, but harmonic vibration, such as vibration internal to the device, induced from within the device, can define nodes at which components can break due to fatigue stress, and can also define anti-nodes that can similarly damage or even batter and damage other components. Therefore, there is a need to control vibration of such components.

By way of an example, this document describes a pre-loaded vibration isolator for an implantable medical device. The pre-loaded vibration isolator can hold the circuit board in place such as to avoid causing fatigue in the feedthrough and battery wires.

In an example, this document describes an apparatus such as an implantable medical device including an implantable biocompatible case. The apparatus can include a component that can be sealed within the case. The apparatus can include a vibration isolator. An at least a portion of the vibration isolator can be situated between components, such as between a case and another component. The vibration isolator can be compressively preloaded, such as to bias against the case and the component.

In an example, this document describes a method of providing a vibration isolator in an implantable medical device. The method can include providing a component sized to be disposed in an implantable biocompatible case. The method can include placing a component in the biocompatible case to define a void between the component and the case. The method can include providing a vibration isolator such that at least a portion of the vibration isolator can fit into the void. The vibration isolator can be subjected to a compressive preload pressure such as to exert a bias against one or both of the case and the component.

The document describes an apparatus such as an implantable medical device including a vibration isolator. The vibration isolator can be shaped to be disposed in a biocompatible device case and to be compressed between the case and a component. The case, the component, and the vibration isolator can be assembled together, and the component and the vibration isolator can be biocompatibly sealed within the case. The vibration isolator can be shaped to exert a preload pressure against each of the case and the component.

BRIEF DESCRIPTION OF THE FIGURES

The drawings illustrate generally, by way of an example, but not by a way of limitation, various embodiments discussed in the present document.

DETAILED DESCRIPTION

Figure 1A:
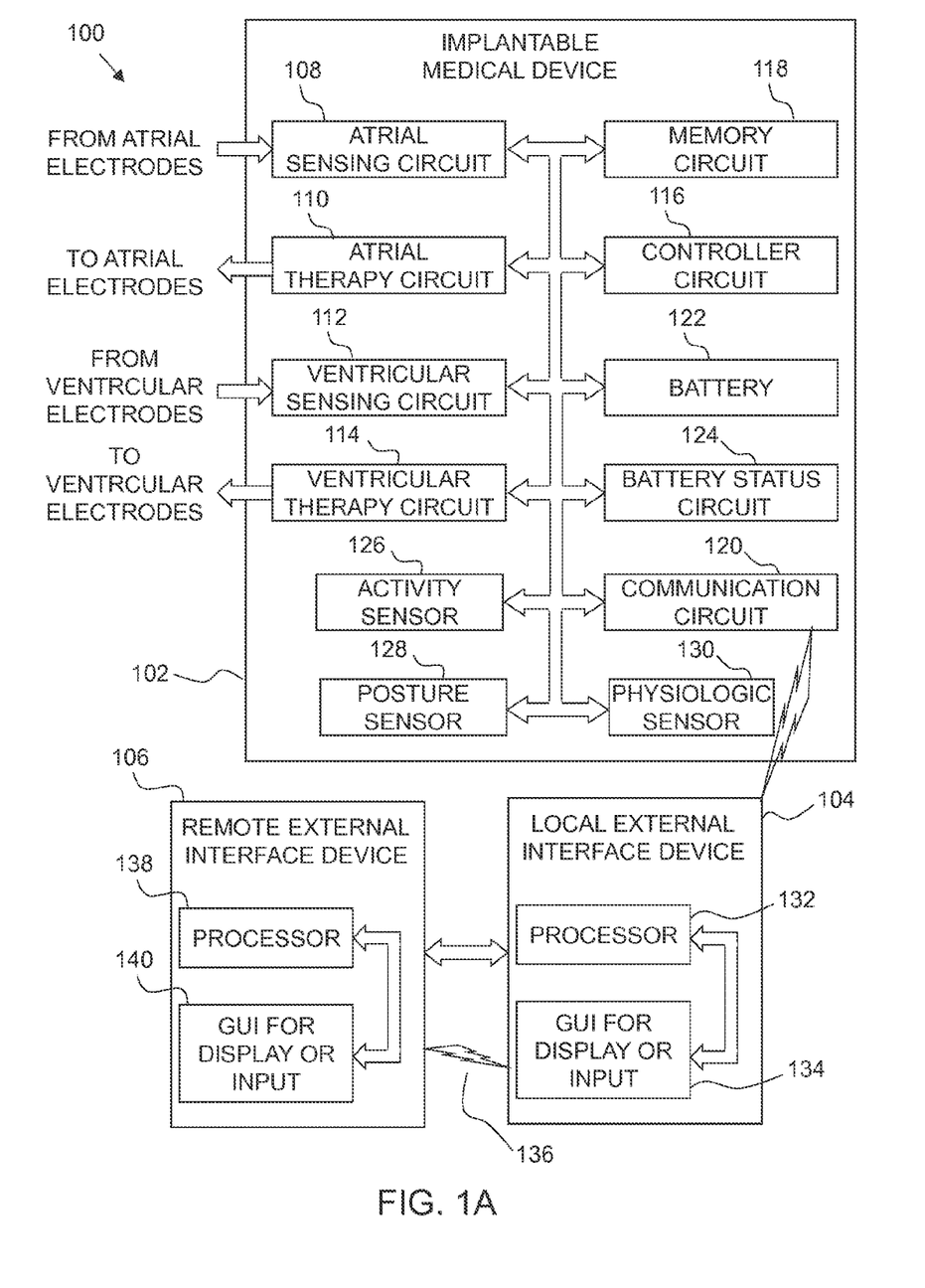
FIGS. 1A-1B illustrate an example of portions of a cardiac function management system and an environment in which it can be used.
Figure 1B:
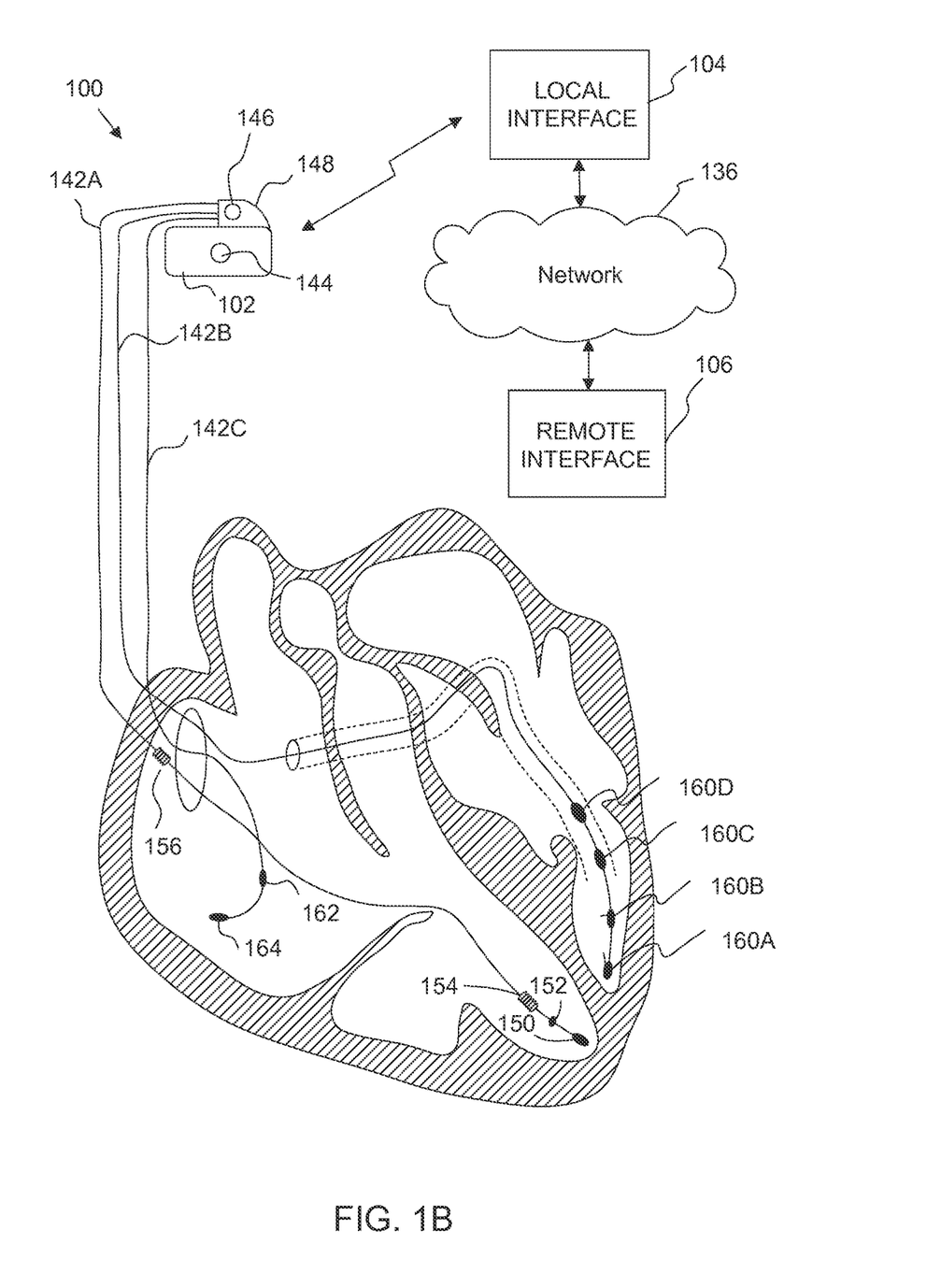

FIGS. 1A-1B show an example of portions of a cardiac function management system 100 and an environment in which it can be used. The system 100 can include an internal vibration isolator, as referenced herein. A vibration isolator can include a resilient support that tends to isolate a system from steady-state excitation and/or from dynamic excitation. As used herein, a vibration isolator can provide one or both of spring properties and damping properties. Damping can include the dissipation of energy with time or distance.

The system 100 can include a medical device for use on an ambulatory patient. The device can be an external (e.g., wearable) medical device or an implantable medical device (IMD) 102, a local external interface device 104, and a remote external interface device 106.

The implantable medical device 102 can optionally include one or more of an atrial sensing circuit 108, an atrial therapy circuit 110, a ventricular sensing circuit 112, a ventricular therapy circuit 114, a controller circuit 116, a memory circuit 118, a communication circuit 120, a power source such as a battery 122, a battery status circuit 124, an activity sensor 126 configured to sense a physical activity signal of a patient or other subject, a posture sensor 128 configured to provide a posture indicative signal, and a physiologic sensor 130 configured to sense a physiologic signal, which is different from the physical activity signal of the subject.

The atrial sensing circuit 108 can include one or more channels and can be coupled to electrodes, such as an intra-atrial electrode or any other electrode that can permit sensing of an intrinsic atrial cardiac signal, including atrial depolarization information. The atrial therapy circuit 110 can include one or more channels and can similarly be coupled to these or other electrodes, such as for delivering pacing pulses, cardiac resynchronization therapy (CRT), cardiac contractility modulation (CCM) therapy, defibrillation/cardioversion shocks, or other energy pulses to one or both atria.

The ventricular sensing circuit 112 can include one or more channels and can be coupled to electrodes, such as an intraventricular electrode, a left ventricular/coronary sinus (LV/CS) electrode, or any other electrode that can permit sensing of an intrinsic ventricular cardiac signal including ventricular depolarization information. The ventricular therapy circuit 114 can include one or more channels and can similarly be coupled to these or other electrodes, such as for delivering pacing pulses, cardiac resynchronization therapy (CRT), cardiac contractility modulation (CCM) therapy, defibrillation/cardioversion shocks, or other energy pulses to one or both ventricles.

The activity sensor 126 can include a single or multiple axis accelerometers, such as to sense an acceleration of the subject that can be indicative of a physical activity of the subject. The activity sensor 126 can also include a sensor interface circuit configured to process the acceleration signal and provide a resulting physical activity signal. The physical activity signal can be indicative of a physical exertion of the subject. The activity sensor 126 can also be used for other purposes, such as to sense the subject's posture, heart sounds, or other information available from an acceleration signal.

The posture sensor 128 can include a tilt-switch, a separate single or multiple axis accelerometers, or other sensors capable of providing the posture-indicative signal. The posture indicative signal can be either directly sensed by the posture sensor 128 or extracted from other physiologic information obtained from the physiologic sensor 130.

The physiologic sensor 130 can include an impedance (or other physiological conductivity characteristic) sensor, a respiration sensor, or another sensor. The physiologic sensor 130 can include a respiration sensor that can sense respiration via physiologic impedance (or other physiological conductivity characteristic) signals that can be provided by an impedance or other sensor. The impedance or other physiological conductivity sensor can include or be coupled to electrodes configured to deliver test energy, such as a sub-capture test energy delivered to the subject's thorax, and to sense a responsive voltage signal, such as an indicator of the thoracic impedance or thoracic conductivity. The resulting thoracic impedance or conductivity signal can be filtered to provide information about respiration, heart contraction, or thoracic fluid accumulation. The electrodes used for impedance monitoring can include one or any combination of one or more right atrial (RA) electrodes, one or more right ventricular (RV) electrodes, one or more LV/CS electrodes (that can be located on a bipolar or quadripolar LV/CS lead), one or more wired or wireless epicardial electrodes, IMD electronics unit housing or header electrodes, or one or more other implantable or wearable electrodes. The impedance monitoring is merely an example of monitoring a physiological conductivity characteristic; other examples of this can include voltage monitoring, transimpedance monitoring, transconductance monitoring, etc.

In various examples, the physiologic sensor 130 can be configured to provide information about heart rate, heart rate variability, autonomic balance, heart vibrations, intracardiac pressure, thoracic fluid status, respiration, patient activity level, temperature, pH, potassium levels, oxygenation, cardiac volumes, blood pressure, or ejection fraction.

A processor or controller circuit 116 can be coupled to the atrial sensing circuit 108 and the ventricular sensing circuit 112, such as to receive information from the sensed cardiac signals. The controller circuit 116 can also be coupled to the activity sensor 126 to receive information about the subject's physical activity or exertion level. The controller circuit 116 can also be coupled to the physiologic sensor 130 such as to receive other physiologic information. Such other physiologic information can include cardiac contraction signal, such as to provide information about the subject's heart rate or interval, stroke volume, or other information available from the cardiac contraction signal. The other physiologic information can include a respiration signal, such as to provide information about the subject's breathing rate or interval, tidal volume, or other information available from the respiration signal.

The controller circuit 116 can include a signal processor circuit, such as a digital signal processor (DSP) circuit, such as for extracting a parameter from which a diagnostic indicator can be generated. The signal processor circuit can include dedicated circuitry for performing one or more signal processing functions. The controller circuit 116 can be coupled to the atrial therapy circuit 110 and the ventricular therapy circuit 114 to provide control or triggering signals, such as to trigger timed delivery of the therapy pulses. The controller circuit 116 can be configured to provide control to help permit therapy to be effectively delivered, such as in combination with one or more other therapies (e.g., bradycardia pacing, antitachyanbythmia pacing (ATP), cardiac resynchronization therapy (CRT), atrial or ventricular defibrillation shock therapy) or functionalities (e.g., autothreshold functionality for automatically determining pacing threshold energy, and autocapture functionality for automatically adjusting pacing energy to capture the heart, etc.). In an example, this can include providing dedicated modules within the controller circuit 116 or providing executable, interpretable, or otherwise performable code to configure the controller circuit 116.

A memory circuit 118 can be included or coupled to the controller circuit 116, such as to store control parameter values, physiological data, or other information. A communication circuit 120 can be coupled to the controller circuit 116 such as to permit radiofrequency (RF) or other wireless communication with an external device, such as the local external interface device 104 or the remote external interface device 106.

The battery 122 can include one or more batteries to provide power to the implantable medical device 102. The battery 122 can be rechargeable, such as by wireless transcutaneous power transmission from an external device to the implantable medical device 102. The battery status circuit 124 can be communicatively coupled to each of the battery 122 and the controller circuit 116, such as to determine battery status information, for example, indicative of how much energy remains stored in the battery 122. The controller circuit 116 can be configured to alter operation of the implantable medical device 102, such as based at least in part on the battery status information.

The local external interface device 104 can include a processor circuit 132 and a graphic user interface (GUI) 134 or similar devices for displaying information or receiving user input as well as a communication circuit, such as to permit wired or wireless communication with the remote external interface device 106 over a communications or computer network 136. Similarly, the remote external interface device 106 can include a processor circuit 138 and a graphic user interface (GUI) 140 or similar devices for displaying information or receiving user input as well as a communication circuit, such as to permit wired or wireless communication with the local external interface device 104 over the communications or computer network 136.

The system 100 includes processing capabilities in the implantable medical device 102 (e.g., provided by the controller circuit 116), the local external interface device 104 (e.g., provided by the processor 132), and the remote external interface device 106 (e.g., provided by the processor 138). Various methods discussed in this document can be implemented at any of such locations, or tasks can be distributed between two or more of such locations.

FIG. 1B shows an example of the implantable medical device 102, which can be coupled to one or more intravascular leads, such as an RV lead 142A, a CS/LV lead 142B, or a right atrial (RA) lead 142C. The implantable device 102 can include a housing electrode 144 that can be located on an external surface of a housing carrying the electronics of the implantable device 102. A header electrode 146 can be located on a header 148 of the implantable medical device 102. The header 148 can extend outward from the housing. The RV lead 142A can include one or more electrodes, such as an RV tip electrode 150, a slightly more proximal RV ring electrode 152, a slightly more proximal RV first coil electrode 154, and a more proximal supraventricular second coil electrode 156. The CS/LV lead 142B can include one or more electrodes, such as electrodes 160A, 160B, 160C, and 160D (arranged distally to proximally), in a quadripolar electrode configuration. The electrodes can be arranged in bipolar or unipolar electrode configurations. The RA lead 142C can include one or more electrodes, such as RA electrodes 162 and 164.

Figure 2:
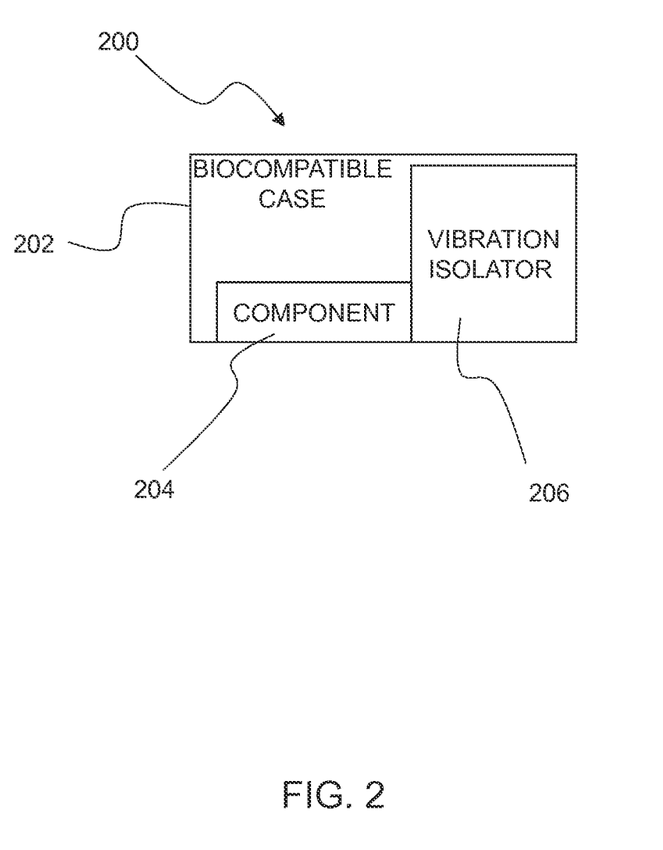
FIG. 2 illustrates a block diagram of an example of an implantable medical device.

FIG. 2 illustrates an example of a block diagram of an example of an implantable medical device 200. The implantable medical device 200 can include an implantable biocompatible case 202, a component 204, and a vibration isolator 206. The component 204 can include a circuit board or other substrate, a battery, a capacitor, or another component. The component 204 can be sealed within the case 202. The circuit board can include a flexible circuit board. The circuit board can include a fiber board. At least a portion of the vibration isolator 206 can be situated between the case 202 and the component 204. The vibration isolator 206 can be compressively preloaded, such as to bias against the case 202 and the component 204. The vibration isolator 206 can be in contact with the component 204 along a selected area.

The vibration isolator 206 can include a silicone material. The silicone can have a nonlinear spring rate. The spring rate can be affected by a damping effect of the material, such as by including higher damping at higher deformation or deformation rate. Accordingly, the silicone can have a first spring rate at a first displacement or first deformation, or first rate of deformation such as at a first vibratory frequency, and can have a higher second spring rate at a second displacement or second deformation or second rate of deformation, such as at a second vibratory frequency. The second frequency can be higher than a first frequency.

The vibration isolator 206 can include at least one of neoprene, rubber, nitrile, silicone or combinations thereof. The vibration isolator 206 can include a material having stiffness that can increase with an increase in deformation such as compression. The vibration isolator 206 can include a viscous damper to damp the vibrations. Viscous damping can be the dissipation of energy that occurs when a particle in a vibrating system is resisted by a force that has a magnitude proportional to the magnitude of the velocity of the particle and the direction opposite to the direction of the particle. The vibration isolator 206 can form a composite including a desiccant. A vibration isolator 206 can be viscoelastic, such as because it includes materials that give it viscoelastic properties. Viscoelasticity is described in "Dynamic viscoelastic properties of experimental silicone soft lining," Dental Materials Journal 2010; 29(4): 454-460, which is incorporated herein by reference in its entirety. The present subject matter can include elastomers, such as those used to provide a vibration isolator 206, that are not viscoelastic, or have a small viscoelasticity.

The vibration isolator 206 can include a coulomb damper to damp the vibrations. Coulomb damping (e.g., dry friction damping) can be the dissipation of energy that occurs when a particle in a vibrating system is resisted by a force, where the magnitude of force can be a constant independent of displacement and velocity, and the direction of force can be opposite to the direction of the velocity of the particle.

The vibration isolator 206 can be subjected to a substantially uniform stress. A portion of the vibration isolator 206 can be stressed more than another portion of the vibration isolator 206.

The vibration isolator 206 can be sized or shaped to conform to an exterior of the component 204, such as before compressive preloading. The vibration isolator 206 can be sized or shaped to conform to an interior of the case 202 before compressive preloading.

The case 202 and the component 204 can define a void between them. A first portion of the vibration isolator 206 can be shaped to fit in the void, such as when the vibration isolator 206 is substantially free of compressive preload. A second portion of the vibration isolator 206 can be subjected to the compressive preload pressure, such as after the first portion is put into the void. The second portion can be semi-circular in shape. The semi-circular portion of the vibration isolator 206 can be selected to be exposed to more stress than another portion of the vibration isolator 206. The semi-circular portion can be coextensive with an adjacent battery or other adjacent component. The semi-circular portion can be sized to be situated adjacent to and within a perimeter of the battery. The second portion of the vibration isolator 206 can be circular. A potting material can be encased within the case 202.

The vibration isolator 206 can be configured to transmit a portion of a vibration motion to which it can be exposed, such as to another component of the implantable medical device 200, such as the case 202.

A first portion of the vibration isolator 206 can include an exterior that has the same shape as the void but that is scaled larger than the void. Accordingly, when located in the void, the vibration insulator 206 can be relatively evenly stressed. The vibration isolator 206 can include a Newtonian or non-Newtonian material.

The case 202, the component 204, and the vibration isolator 206 can be assembled together. The vibration isolator 206 can be disposed in the biocompatible device case 202 and compressed between the case 202 and the component 204. The vibration isolator 206 can be in contact with the component 204 at a selected number of contact points. At least one contact point can include a selected one of a node or an anti-node of the component 204, such as when the vibration isolator 206 is vibrating at a selected frequency, such as at a natural frequency. Natural frequency can be the frequency of free vibration of a system. For a multiple degree of freedom system, the natural frequencies are the frequency of the normal modes of vibration. The node can be a partial node at the selected frequency. A partial node can be the point, line, or surface in a standing-wave system where some characteristic of the wave field has a minimum amplitude differing from zero. The appropriate modifier should be used with the words "partial node" to signify the type that can be intended, e.g., displacement partial node, velocity partial node, and/or pressure partial node. A standing wave can be a periodic wave having a fixed distribution in space, which can be the result of interference of progressive waves of the same frequency and kind. Such waves are characterized by the existence of nodes or partial nodes and antinodes that are fixed in space. An antinode can be a point, line, or surface in a standing wave where some characteristic of the wave field has maximum amplitude. The vibration isolator 206 can be shaped to contact only anti-nodes of the component 204 at the selected frequency.

The vibration isolator 206 can be configured to define one or more recesses that can be sized or shaped to provide a relief for one or more portions of the component 204. The component 204 can include a circuit board including a plurality of elements coupled thereto. At least one of the elements can be sized or shaped and located to be disposed in the one or more recesses, while the vibration isolator 206 can be subjected to the compressive preload pressure, such as to exert the bias against each of the case 202 and the component 204.

The vibration isolator 206 can be shaped to physically contact edges of the case 202 or of the component 204. The vibration isolator 206 can be shaped to selectively contact one or more nodes, anti-nodes, or spaces there-between of at least one vibration mode. In a system undergoing vibration, a mode of vibration can be a characteristic pattern assumed by the system in which the motion of every particle is simple harmonic with the same frequency. Two or more modes may exist concurrently in a multiple degree-of-freedom system. The vibration isolator 206 can be configured to damp motion of the case 202 with respect to the component 204. The vibration isolator 206 can have a damping coefficient selected to at least critically dampen vibration of at least a portion of the component 204 with respect to the case 202. A frequency of the vibration can be from around 10 hertz to 6000 hertz. The vibration isolator 206 can include a snubber. The snubber is a device that can be used to increase the stiffness of a system, such as an elastic system. The snubber can increase stiffness by a large factor. A snubber can increase stiffness when a displacement becomes large, for example, when it exceeds a threshold.

The component 204 can be sized to be disposed in an implantable biocompatible case 202 to define a void between them. A vibration isolator 206 can be provided such that a portion of the vibration isolator 206 can fit into the void while subjected to a compressive preload pressure, such as to exert a bias against each of the case 202 and the component 204.

Figure 3A:
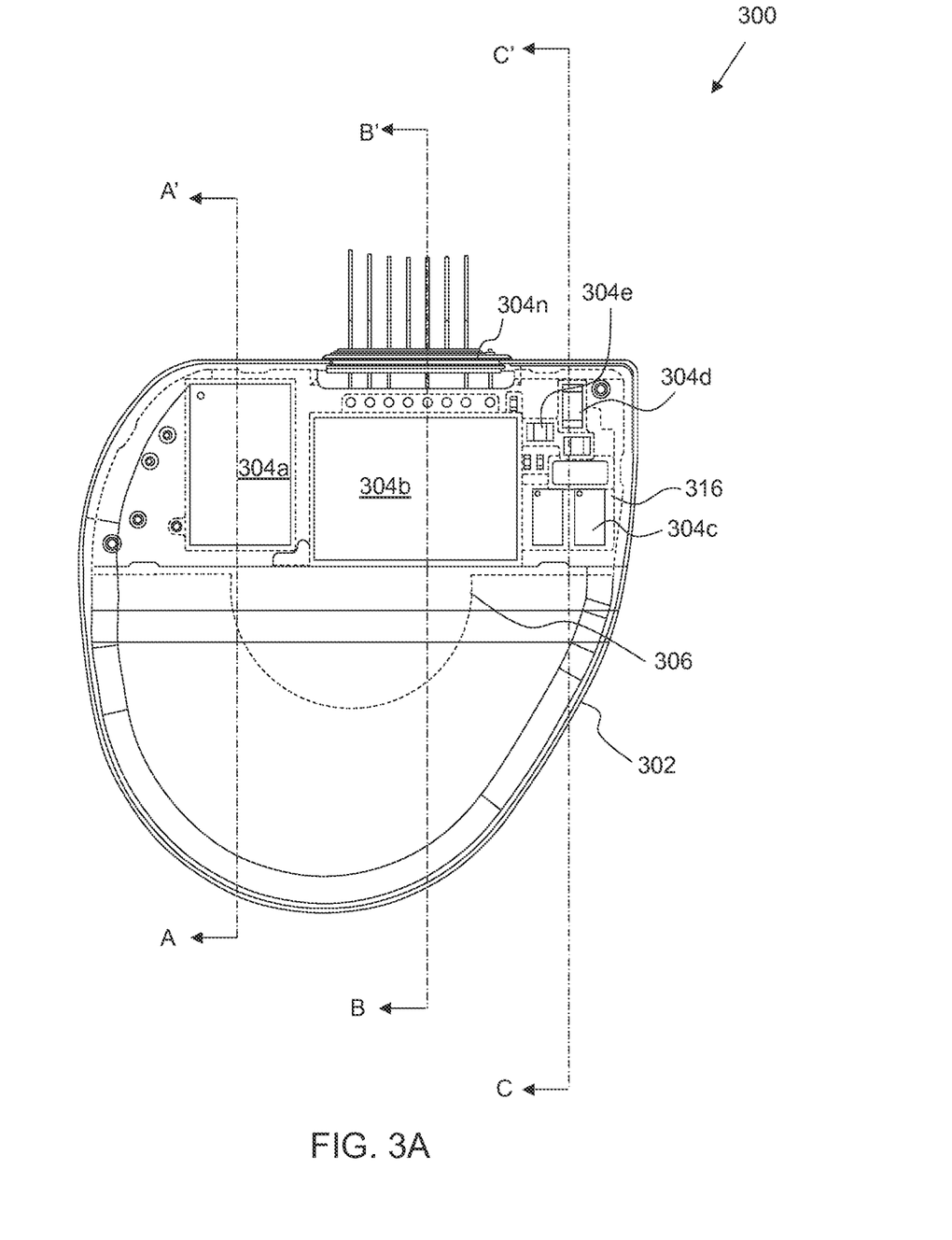
FIG. 3A is a schematic cutaway diagram of an example of an implantable medical device.

FIG. 3A shows a schematic cutaway diagram illustrating the implantable medical device 300. The implantable medical device 300 can include an implantable biocompatible case 302 and one or more components such as a component 304a, a component 304b, a component 304c, a component 304d, a component 304e, and a component 304n (collectively referred to herein as components 304). The one or more components 304 can include active or passive components. Examples of the components 304 can include integrated circuit chips such as application specific integrated circuit (ASIC) chips, a feedthrough assembly, and one or more diodes, amplifiers, transistors, oscillators, resistors, capacitors, inductors, transformers, RF transmitter/receiver, interconnects, or the like. The components 304 can be used to perform the intended one or more operations associated with the implantable medical device 300. The implantable medical device 300 can include a circuit board 316 on which the various individual components 304 can be mounted. The circuit board 316 can include a flexible circuit board or a rigid circuit board such as a pre-impregnated composite. The one or more components can be sealed within the case 302.

The implantable medical device 300 can include a vibration isolator 306 (shown with the dotted line). At least a portion of the vibration isolator 306 can be situated between the case 302 and the component 304, and compressively preloaded such as to bias against the case 302 and the component 304. As shown in FIG. 3, one or more of the components 304 can be enclosed by the vibration isolator 306 such as to protect such components 304 from shocks or vibrations.

Figure 3B:
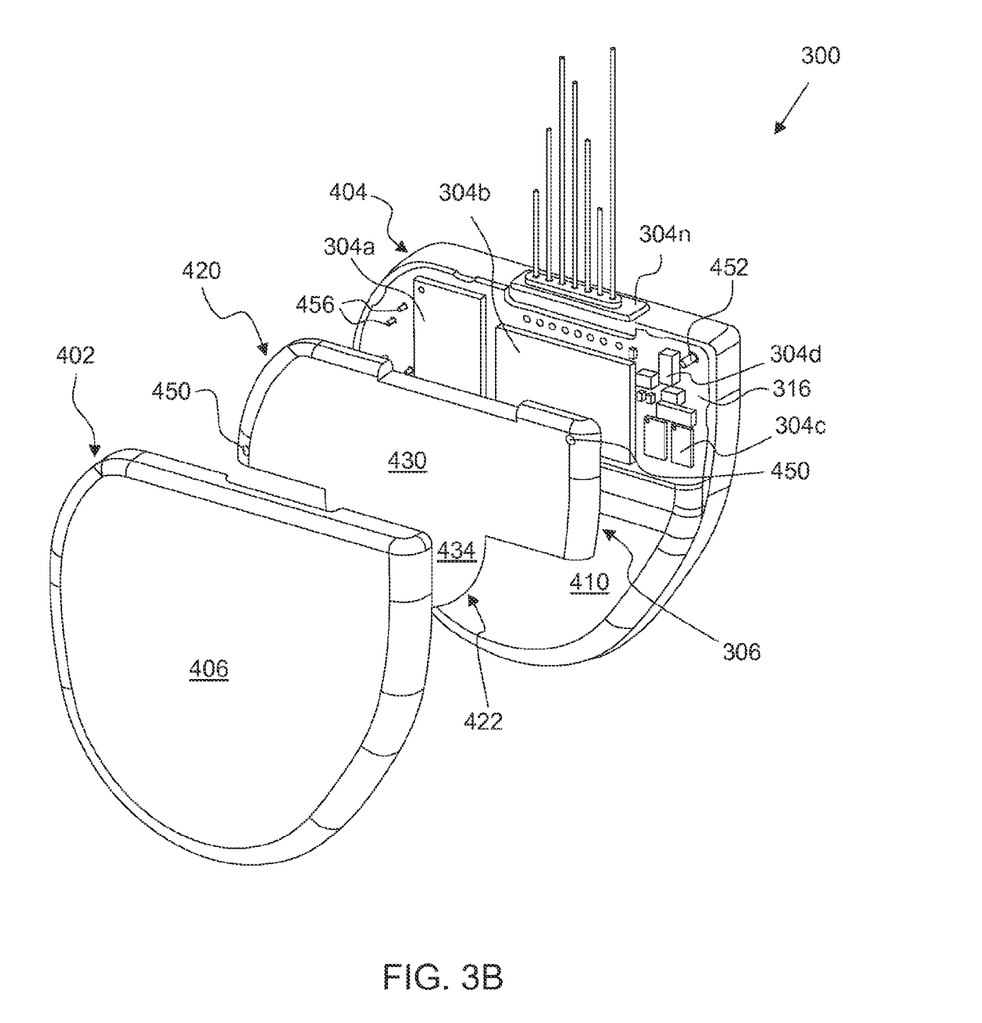
FIG. 3B is an exploded front perspective view of an example of the implantable medical device.
Figure 3C:
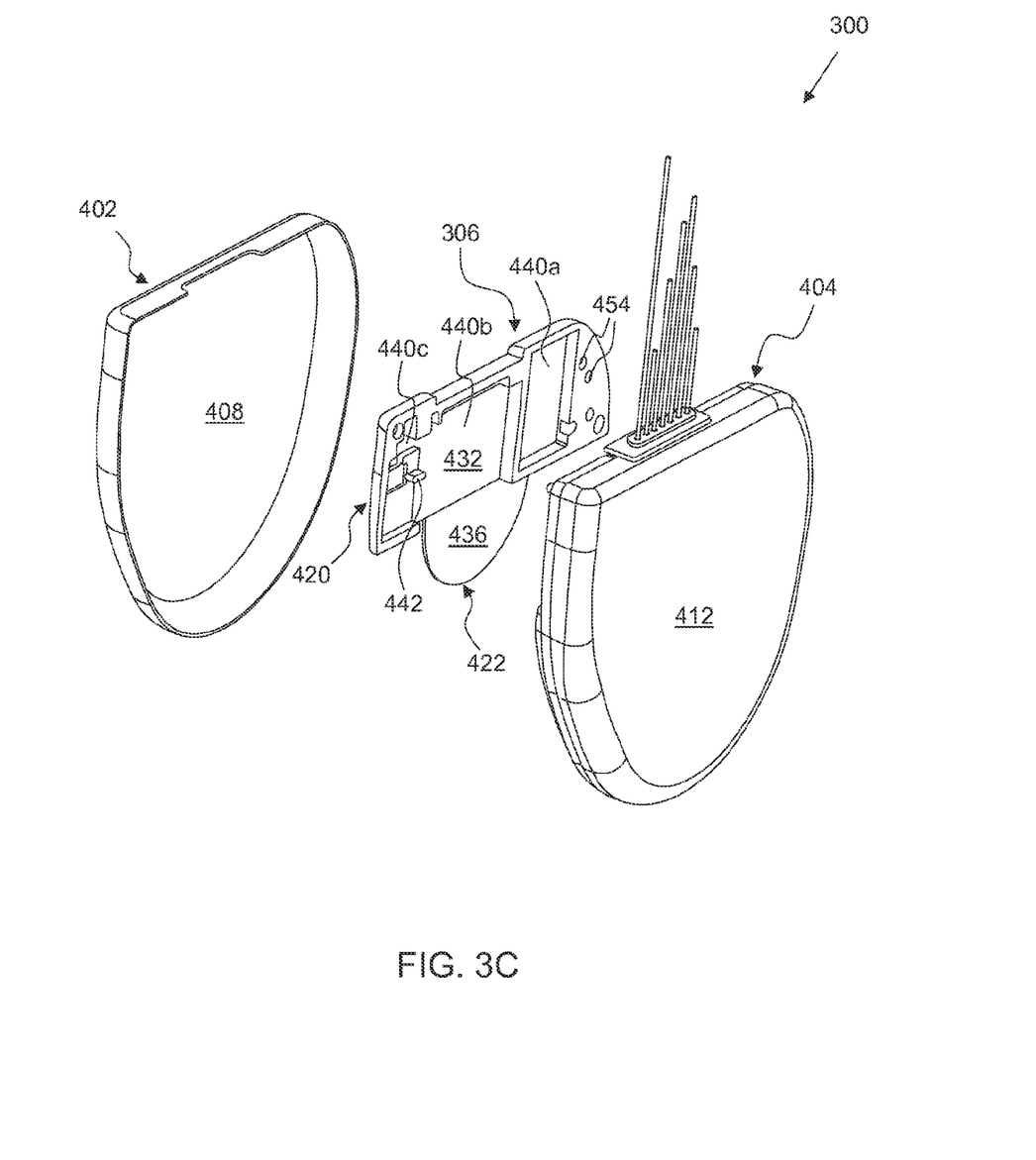
FIG. 3C is an exploded rear perspective view of the example of the implantable medical device.

Referring now to FIG. 3B-3C, exploded perspective views of the implantable medical device 300 are illustrated. FIG. 3B illustrates an exploded front perspective view of the implantable medical device 300. FIG. 3C illustrates an exploded rear perspective view of the implantable medical device 300. The case 302 (shown in FIG. 3A) can include a first half 402 and a second half 404. The first half 402 of the case 302 can include an exterior surface 406 and an interior surface 408. The second half 404 of the case 302 can include an interior surface 410 and an exterior surface 412. The interior surface 410 of the second half 404 can be defined by components 304. The interior surface 410 can include the circuit board 316 supporting the components 304 thereon. The circuit board 316 can be configured to conform to a periphery of an upper portion of the interior surface 410 such that the circuit board 316 can be mounted on the upper portion of the interior surface 410 of the second half 404.

The first half 402 can enclose the components 304, such as when they are mounted on the circuit board 316, such as when they are biocompatibly sealed with the second half 404. The first half 402 and the components 304 can define a void therebetween, such as when the first half 402 is biocompatibly sealed with the second half 404. The vibration isolator 306 can be disposed in the void. The vibration isolator 306 can include a first portion 420 and a second portion 422 integral with the first portion 420. The first portion 420 can include a front surface 430 and a rear surface 432, and the second portion 422 can include a front surface 434 and a rear surface 436. An outer periphery of the vibration isolator 306 can be shaped to conform to the interior surface 408 of the first half 402. A front surface (e.g., the front surfaces 430 and 434 of the first and second portions 420 and 422) of the vibration isolator 306 can be shaped to conform to the interior surface 408 of the first half 402. A rear surface (e.g., the rear surfaces 432 and 436 of the first and second portions 420 and 422) of the vibration isolator 306 can be shaped to conform to an exterior of one or more components 304. The rear surface 432 of the first portion 420 of vibration isolator 306 can include one or more recesses 440a, 440b, and 440c (collectively referred to as recesses 440) shaped to provide relief to an exterior of the components 304. The one or more recesses 440 of the rear surface 432 can be configured to receive the components 304, such as when they are protruding from the circuit board 316. The rear surface 432 of the first portion 420 can include one or more protrusions 442 such as to conform to the exterior of the one or more components 304. The one or more protrusions 442 of the rear surface 432 can be configured to be received by depressions between the one or more components 304.

The second portion 422 of the vibration isolator 306 can include a semi-circular shape. The front surface 434 and the rear surface 436 of the second portion 422 can include flat surfaces, such as those generally free from recessions or protrusions. The second portion 422 can include a flat semi-circular structure, integral with the first portion 420 of the vibration isolator 306. A diameter of the semi-circular second portion 424 can be smaller as compared to a length of the first portion 420. The diameter of the second portion 424 can be same as the length of the first portion 420. The semi-circular second portion 424 can be coextensive with an adjacent battery or other adjacent component. The semi-circular second portion 424 can be sized to be situated adjacent to and within a perimeter of the adjacent battery. The second portion 424 can include an arcuate shape. A thickness of the second portion 424 can be substantially smaller as compared to a thickness of the first portion 420.

The vibration isolator 306 can be mounted on the second half 404 of the case 302 such that the second portion 422 of the vibration isolator 306 encloses the components 304. The vibration isolator 306 can include one or more through holes 450, such as extending from the front surface 430 to the rear surface 432 of the first portion 420. The through holes 450 can respectively receive one or more pins 452 protruding from the interior surface 410 of the second half 404, such as to affix the vibration isolator 306 with the second half 404 and to enclose the components 304. The rear surface 432 of the first portion 422 can include circular recesses 454 adapted to respectively receive one or more pins 456 protruding from the interior surface 410 of the second half 404. The recesses 454 and the pins 456 can facilitate affixing the vibration isolator 306 with the second half 404 and to enclose the components 304.

Figures 3D, 3E, 3F:
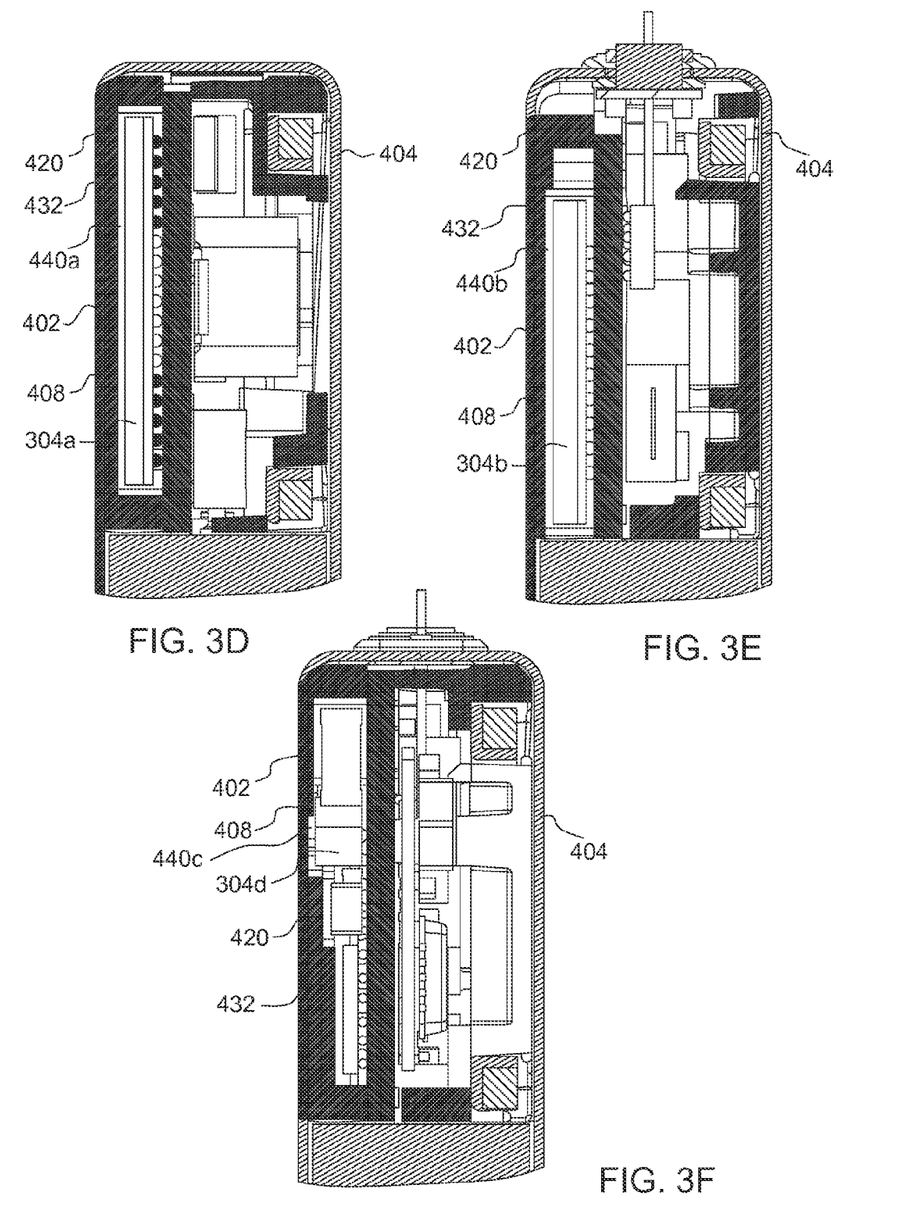
FIGS. 3D-3F illustrate an example of cross-sectional views of the implantable medical device of FIG. 3 along lines A, B and C.

Referring now to FIGS. 3D-3F, cross-section views of the implantable medical device 300 of FIG. 3 along lines A-A', B-B', and C-C' are illustrated. FIG. 3D illustrates a cross-section view of the implantable medical device 300 along the line A-A', which is positioned at a substantial left side on the device 300. FIG. 3D particularly illustrates the cross-section view of an upper left portion of the device 300. As shown, the first half 402 and the second half 404 of the case 302 can enclose the first portion 420 and the component 304a. The interior surface 408 of the first half 402 can enclose the first portion 420 of the vibration isolator 306, and the first portion 420 of the vibration isolator 306 can enclose the component 304a. For example, one of the recesses 440a of the rear surface 432 of the first portion 420 can be seen accommodating the component 304a therein.

FIG. 3E illustrates a cross-section view of the implantable medical device 300 along the line B-B', which is positioned at a substantial intermediate portion on the device 300. FIG. 3E particularly illustrates the cross-section view of an intermediate upper portion of the device 300. As shown, the first half 402 and the second half 404 of the case 302 can enclose the first portion 420 of the vibration isolator 306 and the component 304b. The interior surface 408 of the first half 402 can enclose the first portion 420 of the vibration isolator 306, and the first portion 420 of the vibration isolator 306 can enclose the component 304b. For example, one of the recesses 440b of the rear surface 432 of the first portion 420 can be seen accommodating the component 304b therein.

FIG. 3F illustrates a cross-section view of the implantable medical device 300 along the line C-C', which is positioned at a substantial right side of the device 300. FIG. 3F particularly illustrates the cross-section view of an upper right portion of the device 300. As shown, the first half 402 and the second half 404 of the case 302 can enclose the first portion 420 of the vibration isolator 306 and the component 304d. The interior surface 408 of the first half 402 can enclose the first portion 420 of the vibration isolator 306, and the first portion 420 of the vibration isolator 306 can enclose the component 304d. For example, one of the recesses 440c of the rear surface 432 of the first portion 420 can be seen accommodating the component 304d therein.

The vibration isolator 306 can be configured to conform to the interior surface 408 of the first half 402 and the exterior of the component 304 without compressively preloading. The vibration isolator 306 can be subjected to a compressive preload pressure such as to exert a bias against each of the case 302 and the component 304, such as when the first half 402 biocompatibly sealed with the second half 404 and the vibration isolator 306 encloses the components 304. The first half 402 and the components 304 can define the void there-between when the first half 402 is biocompatibly sealed with the second half 404. At least a portion of the vibration isolator 306 can be situated between and compressively preloaded to bias against the case 302 and the component 304. The first portion 420 of the vibration isolator 306 can be shaped to fit into the void substantially free of compressive preload, and the second portion 422 of the vibration isolator 306 can be subjected to the compressive preload pressure. The second portion 422 of the vibration isolator 306 can be exposed to more stress than the first portion 420 of the vibration isolator 306. The compressively preloaded vibration isolator 306 can isolate the components from the shocks and vibrations.

Figure 4:
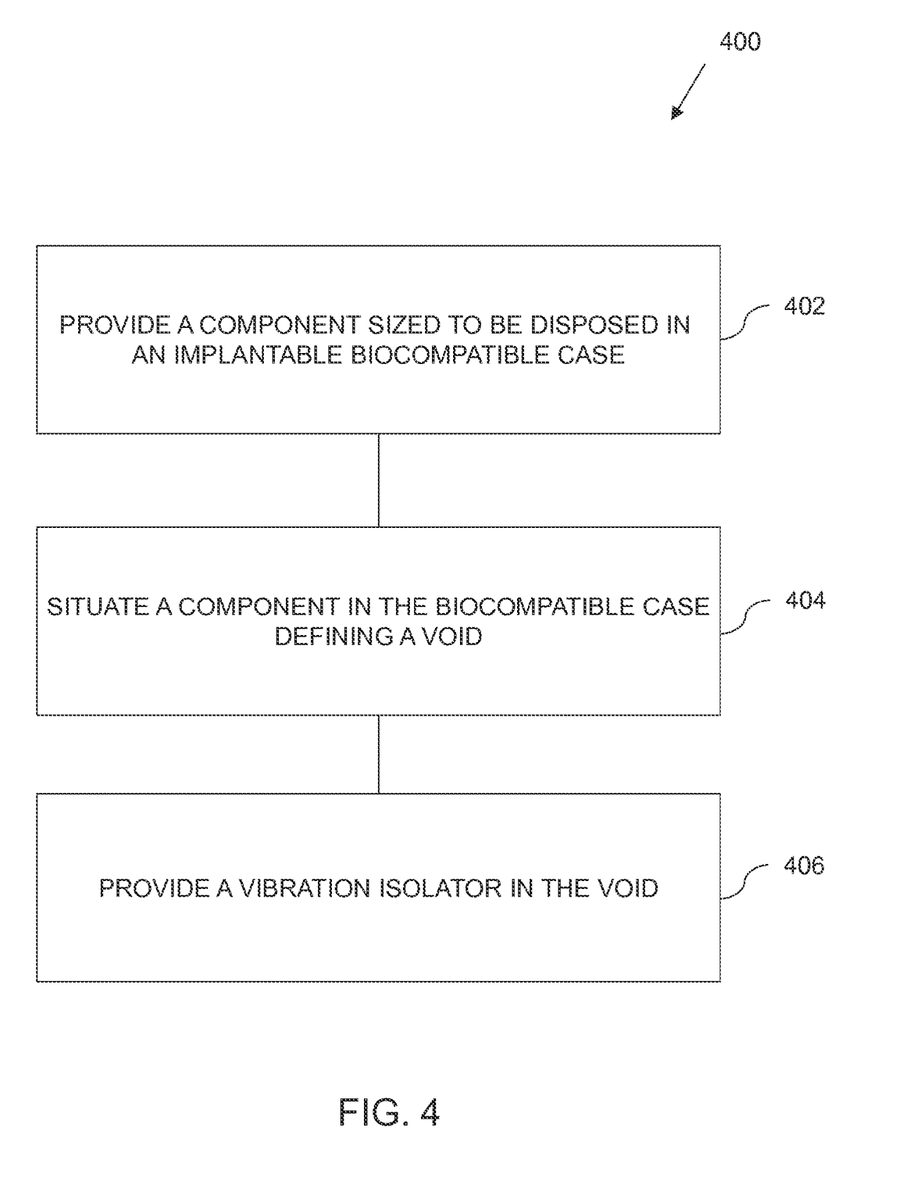
FIG. 4 is a diagram of an example of a method of preventing a component of the implantable medical device against an external loading.

FIG. 4 is a diagram of a method 400 of preventing the component 304 of the implantable medical device 300 against an external loading. At 402, the component 304 sized to be disposed in the implantably biocompatible case 302 can be provided. The component 304 can include one or more of an integrated circuit (IC) chip, feedthrough assembly, and one or more diodes, amplifiers, transistors, oscillators, resistors, capacitors, inductors, transformers, RF transmitter/receiver, interconnects, and the like such as to perform the intended one or more operations associated with the implantable medical device 300. At 404, the component 304 can be situated in the biocompatible case 302. The component 304 can be mounted on a circuit board and placed within the case 302. The component 304 and the biocompatible case 302 can define a void between them.

At 406, the vibration isolator 306 can be provided such that a portion of the vibration isolator 306 can fit into the void and can be subjected to a compressive preload pressure for exerting a bias against each of the case 302 and the component 304.

The vibration isolator 306 can be provided by disposing a liquid in the biocompatible case 302.

The method 400 can include determining one or more vibration modes. In an example, determining vibration modes can include determining a natural frequency of the component. The method 400 can include providing a material of the vibration isolator 306 and the material can be selected corresponding to the component 304. The material can be selected using the natural frequency of the component 304.

The method 400 can include providing the vibration isolator 306 with a selected damping coefficient for at least the critically damping vibration of the component 304 with respect to the case 302. The method 400 can provide the vibration isolator 306 with a selected damping coefficient for under-damping vibration of the component 304 with respect to the case 302. The vibration isolator 306 with a selected damping coefficient can be provided for overdamping vibration of the component 304 with respect to the case 302. The vibration isolator 306 with a selected damping coefficient can be provided to snub a vibration motion of the component 304.

The method 400 can include disposing of the vibration isolator 306 between two case portions (for example, first half 402 and the second half 404 of the biocompatible case 302) and pressing the case portions together. The method 400 can include shaping the vibration isolator 306 in a manner such that a portion (e.g., a first portion 420) of the vibration isolator 306 can fit into the void out of contact with one of the case 302 and the component 304. Another portion of the vibration isolator 306 (e.g., a second portion 422 of the vibration isolator 306) can be subjected to a compressive preload pressure, thereby exerting a bias against each of the case 302 and the component 304.

The method 400 can include disposing the vibration isolator 306 between two case portions of the biocompatible case 302 and pressing the case portions together. The vibration isolator 306 and the biocompatible case 302 can be disposed in a humidity controlled chamber before disposing the vibration isolator 306 in the biocompatible case 302. A humidity controlled chamber can be a clear room. A humidity controlled chamber can be a chamber sized large enough to receive at least one implantable medical device.

The subject matter can offer various advantages, such as including allowing looser tolerance on other components because the vibration isolator can absorb movement. Examples can allow greater tolerance ranges since the vibration isolator can help accommodate these dimensional changes. A vibration isolator including silicone can exhibit low creep/compression set, high dielectric value, high stability, and an ability to accept a filler (e.g., a desiccant).

Silicone and polyurethane can be used to pot all or a portion of the vacant regions of an interior of an implantable medical device, such as to help provide temperature stability, such as to resist damage during solder reflow, to provide a high dielectric constant, or to provide a thermal coefficient of expansion ("TCE") close to materials used in the electronics.

Vibration isolators such as silicone isolators can isolate the circuit board and components from vibration (e.g., via viscous damping). Pre-loaded silicone can provide a uniform support of or pressure on the circuit board. This can limit component motion during resonance e.g. snub motion). The isolator can work as a snubber since it had flush contact with the circuit board and (in many cases) has increased stiffness with the frequency.

Various Notes & Examples

Example 1 can include subject matter such as a system, apparatus, method, tangible machine readable medium, etc.) that can include a vibration isolator. The subject matter can include an implantably biocompatible case. The subject matter can also include a component, such as circuitry, a battery, a capacitor, and the like. The component can be sealed within the case. The subject matter can include a vibration isolator, at least a portion of which is situated between and compressively preloaded to bias against the case and the component.

In Example 2, the subject matter of Example 1 can optionally be configured such that the vibration isolator can include a material that can have increasing stiffness with increasing compression.

In Example 3, the subject matter of any of Examples 1-2 can optionally be configured such that the vibration isolator can be in contact with the component along a selected area of a selected magnitude.

In Example 4, the subject matter of any of Examples 1-3 can be optionally configured such that the vibration isolator can behave as a viscous damper.

In Example 5, the subject matter of any of Examples 1-4 can optionally be configured such that the vibration isolator can behave as a coulomb damper.

In Example 6, the subject matter of any of Examples 1-5 can optionally be configured such that the vibration isolator can be subject to a substantially uniform stress throughout.

In Example 7, the subject matter of any of Examples 1-6 can optionally be configured such that a portion of the vibration isolator can be stressed more highly than another portion of the vibration isolator.

In Example 8, the subject matter of any of Examples 1-7 can optional be configured such that the component can include a circuit board.

In Example 9, the subject matter of Example 8 can optionally be configured such that the circuit board can include a flexible circuit board.

In Example 10, the subject matter of any of Examples 8-9 can optionally be configured such that the circuit board can include a fiber board.

In Example 11, the subject matter of any of Examples 8-9 can optionally be configured such that the vibration isolator can include silicone.

In Example 12, the subject matter of Example 11 can optionally be configured such that the silicone can include a desiccant.

In Example 13, the subject matter of any of Examples 11-12 can optionally be configured such that the silicone can have a nonlinear spring rate that can be higher at a second frequency that is higher than a first frequency.

In Example 14, the subject matter of any of Examples 8-13 can optionally be configured such that the vibration isolator can include at least one of neoprene, rubber, nitrite, silicone and combinations thereof.

In Example 15, the subject matter of any of Examples 1-14 can optionally be configured such that the vibration isolator can be shaped to conform to an exterior of the component before compressively preloading.

In Example 16, the subject matter of Example 15 can optionally be configured such that the vibration isolator can be shaped to conform to an interior of the case before compressively preloading.

In Example 17, the subject matter of any of Examples 1-16 can optionally be configured such that the case and the component can define a void between them, and a first portion of the vibration isolator can be shaped to fit in the void substantially free of compressive preload, with a second portion of the vibration isolator subject to the compressive preload pressure.

In Example 18, the subject matter of Example 17 can optionally be configured such that the second portion is semicircular.

In Example 19, the subject matter of Example 18 can optionally be configured such that the portion of the vibration isolator that is semi-circular can be selected to be exposed to more stress than another portion of the vibration isolator.

In Example 20, the subject matter of any of Examples 18-19 can optionally be configured such that the semi-circular portion can be coextensive with an adjacent battery or other adjacent component.

In Example 21, the subject matter of any of Examples 18-20 can optionally be configured such that the semi-circular portion can be sized to be situated adjacent to and within a perimeter of an adjacent battery.

In Example 22, the subject matter of any of Examples 17-21 can optionally be configured such that the second portion can be circular.

In Example 23, the subject matter of any of Examples 17-22, can optionally comprise a potting material encased within the case.

In Example 24, the subject matter of any of Examples 1-23 can optionally be configured such that the vibration isolator can be configured to transmit a portion of a vibration motion to which it is exposed.

In Example 25, the subject matter of any of Examples 1-24 can optionally be configured such that the vibration isolator can be configured to transmit a portion of vibration to another component of the apparatus.

In Example 26, the subject matter of Example 25 can optionally be configured such that the other component can be the case.

In Example 27, the subject matter of any of Examples 1-26 can optionally be configured such that the case and the component can define a void between them, and a first portion of the vibration isolator can have an exterior of the same shape as the void but scaled larger than the void.

In Example 28, the subject matter of any of Examples 1-27 can optionally be configured such that the vibration isolator can include a Newtonian material.

In Example 29, the subject matter of any of Examples 1-28 can optionally be configure such that the vibration isolator can include a non-Newtonian material.

Example 30 can include, or can be combined with any one of Examples 1-29 to include, subject matter (such as a system, apparatus, method, tangible machine readable medium, etc.) that can include a vibration isolator shaped to be disposed in a biocompatible device case and to be compressed between the case and a component while the case, the component and the vibration isolator are assembled together and the component and the vibration isolator are biocompatibly sealed within the case, the vibration isolator shaped to exert a preload pressure against each of the case and the component.

In Example 31, the subject matter of Example 30 can optionally be configured such that the vibration isolator can be in contact with the component at a selected number of contact points.

In Example 32, the subject matter of any of Examples 30-31 can optionally be configured such that at least one contact point can include a one of a node and an anti-node of the component at a selected natural frequency.

In Example 33, the subject matter of Example 32 can optionally be configured such that the vibration isolator can be shaped to contact only anti-nodes of the component.

In Example 34, the subject matter of any of Examples 30-33 can optionally be configured such that the vibration isolator can define one or more recesses shaped to provide a relief for portions of the component while the vibration isolator is subject to a compressive preload pressure exerting a bias against each of the case and the component.

In Example 35, the subject matter of Example 34 can optionally be configured such that the component can include a circuit board comprising a plurality of elements coupled thereto, with at least one of the elements that can be shaped and located to be disposed in the one or more recesses while the vibration isolator can be subject to a compressive preload pressure exerting a bias against each of the case and the component.

In Example 36, the subject matter of any of Examples 30-35 can optionally be configured such that the vibration isolator is shaped to physically contact edges of the component.

In Example 37, the subject matter of Example 36 can optionally be configured such that the vibration isolator can be shaped to physically contact only the edges of the component.

In Example 38, the subject matter of any of Examples 30-37 can optionally be configured such that the vibration isolator can be shaped to contact nodes, anti-node, and spaces therebetween of at least one vibrational mode.

In Example 39, the subject matter of any of Examples 30-38 can optionally be configured such that the vibration isolator can be configured to damp motion of the case with respect to the component.

In Example 40, the subject matter of Example 39 can optionally be configured such that the vibration isolator can have a damping coefficient selected to at least critically damp vibration of at least a portion of the component with respect to the case.

In Example 41, the subject matter of Example 40 can optionally be configured such that a frequency of the vibration is from around 100 hertz to 6000 hertz.

In Example 42, the subject matter of any of Examples 30-41 can optionally be configured such that the vibration isolator includes a snubber.

Example 43 can include, or can be combined with any of the Examples 1-42 to include subject matter that can include (such as a system, apparatus, method, tangible machine readable medium, etc.) providing a component sized to be disposed in an implantably biocompatible case, situating a component in the biocompatible case, with the component and the biocompatible case defining avoid between them. The subject matter can include providing a vibration isolator such that a portion of the vibration isolator fits into the void subject to a compressive preload pressure while exerting a bias against each of the case and the component.

In Example 44, the subject matter of any of Example 43 can optionally be configured such that determining on or more vibration modes includes determining a natural frequency of the component.

In Example 45, the subject matter of any of Examples 43-44 can optionally be configured such that determining one or more vibration modes includes determining several modes.

In Example 46, the subject matter of any of Examples 43-45 can optionally be configured such that providing the vibration isolator can includes disposing a liquid in the case.

In Example 47, the subject matter of any of Examples 43-46 can optionally include shaping the vibration isolator such that a portion of the vibration isolator can fit into the void out of contact with one of the case and the component while another portion is subject to a compressive preload pressure and exerting a bias against each of the case and the component.

In Example 48, the subject matter of any of Examples 43-47, can optionally include providing a material of the vibration isolator that can be selected for damping motion of the case with respect to the component.

In Example 49, the subject matter of any of Examples 43-48, can optionally comprise providing the vibration isolator with a selected damping coefficient for at least critically damping vibration of the component with respect to the case.

In Example 50, the subject matter of any of Examples 43-48, can include providing the vibration isolator with a selected damping coefficient for underdamping vibration of the component with respect to the case.

In Example 51, the subject matter of any of Examples 43-50, can optionally include providing the vibration isolator with a selected damping coefficient for overdamping vibration of the component with respect to the case.

In Example 52, the subject matter of any of Examples 43-51, can optionally include providing the vibration isolator with a selected damping to snub a vibration motion of the component.

In Example 53, the subject matter of any of Examples 43-52, can optionally include disposing the vibration isolator in a biocompatible case.

In Example 54, the subject matter of Example 53 can optionally include disposing the vibration isolator between two case portions of the biocompatible case, and pressing the case portions together.

In Example 55, the subject matter of any of Examples 43-54 can optionally be configured such that disposing the vibration isolator in the biocompatible case includes disposing the vibration isolator and the biocompatible case in a chamber in which humidity is controlled to being below a selected level, before disposing the vibration isolator in the biocompatible case. Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. The code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. The above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An apparatus, comprising:
an implantable biocompatible case having a first case half and a second case half;
a component, sealed within the case, the component including a circuit board coupled to and in direct contact with an interior surface of the second case half; and
a vibration isolator including silicone, at least a portion of which is situated between and compressively preloaded to bias against the first case half and the component.

2. The apparatus of claim 1, wherein the silicone has a nonlinear spring rate that is higher at a second frequency as compared to the nonlinear spring rate at a first frequency.

3. The apparatus of claim 1, wherein the silicone includes a desiccant.

4. The apparatus of claim 1, wherein the circuit board includes at least one of fiber board, flex circuit and ceramic substrate.

5. The apparatus of claim 1, wherein the vibration isolator includes at least one of neoprene, rubber, or nitrile.

6. The apparatus of claim 1, wherein the vibration isolator is shaped to conform to an exterior of the component before compressively preloading.

7. The apparatus of claim 6, wherein the vibration isolator is shaped to conform to the interior of the second case half before compressively preloading.

8. The apparatus of claim 1, wherein the case and the component define a void between them, and a first portion of the vibration isolator is shaped to fit in the void substantially free of compressive preload, with a second portion of the vibration isolator subject to the compressive preload pressure.

9. The apparatus of claim 8, wherein the first portion includes a first front surface and a first rear surface and the second portion includes a second front surface and a second rear surface, wherein the first front surface, the second front surface, and the second rear surface are substantially flat surfaces free from recessions and protrusions, and wherein the first rear surface includes at least one of recessions and protrusions.

10. The apparatus of claim 1, comprising a potting material encased within the implantable biocompatible case.

11. The apparatus of claim 1, wherein the vibration isolator is configured to transmit a portion of a vibration to another component of the apparatus.

12. A method, comprising:
providing a component sized to be disposed in an implantable biocompatible case, the implantable biocompatible case having a first case half and a second case half;
coupling at least a portion of the component to an interior surface of the first case half in the biocompatible case such that the portion of the component is in direct contact with the interior surface, the component and the implantable biocompatible case defining a void between them; and
providing a vibration isolator including silicone, wherein a portion of the vibration isolator fits into the void subject to a compressive preload pressure while exerting a bias against each of the second case half and the component.

13. The method of claim 12, comprising shaping the vibration isolator such that a first portion of the vibration isolator can fit into the void out of contact with one of the second case half and the component while another portion is subject to a compressive preload pressure and exerting a bias against each of the second case half and the component.

14. The method of claim 12, including disposing the vibration isolator between the first case half and the second case half of the implantable biocompatible case, and pressing the first case half and the second case half together.

15. The method of claim 12, wherein disposing the vibration isolator in the implantable biocompatible case includes disposing the vibration isolator and the implantable biocompatible case in a chamber in which humidity is controlled to being below a selected level, before disposing the vibration isolator in the biocompatible case.

16. An apparatus, comprising:
a vibration isolator shaped to be disposed in a biocompatible device case having a first case half and a second case half, the vibration isolator to be compressed between the first case half and a component while the biocompatible device case, the component, and the vibration isolator are assembled together and the component and the vibration isolator are biocompatibly sealed within the biocompatible case, at least a portion of the component coupled to the second case half, and the vibration isolator shaped to exert a preload pressure against each of the first case half and the component, wherein the vibration isolator is in contact with the component at a selected number of contact points, and wherein at least one contact point includes one of a node and an anti-node of the component at a selected natural frequency.

17. The apparatus of claim 16, wherein the vibration isolator defines one or more recesses shaped to provide a relief for portions of the component while the vibration isolator is subject to a compressive preload pressure exerting a bias against each of the first case half and the component.

18. The apparatus of claim 17, wherein the vibration isolator is shaped to physically contact edges of the component.

19. The apparatus of claim 16, wherein the vibration isolator is shaped to contact nodes, anti-node and spaces therebetween of at least one vibrational node.

* * * * *